United States Patent [19]
Singh et al.

[11] Patent Number: 5,759,579
[45] Date of Patent: Jun. 2, 1998

[54] PHARMACEUTICAL SUSPENSION SYSTEMS

[75] Inventors: Kiran Pal Singh, Deptford; Shankar D. Popli, Marlton, both of N.J.

[73] Assignee: American Home Products Corporation, Madison, N.J.

[21] Appl. No.: 702,777

[22] Filed: Dec. 5, 1996

[51] Int. Cl.[6] .................... A61K 9/14; A61K 31/70; A01N 43/04
[52] U.S. Cl. .................... 424/485; 424/484; 424/488; 514/23; 514/54
[58] Field of Search .................... 514/23, 54, 781, 514/782, 450; 424/474, 479, 481, 484, 485, 488

[56] References Cited

U.S. PATENT DOCUMENTS

| | | | |
|---|---|---|---|
| 4,851,232 | 7/1989 | Urquart et al. | 424/469 |
| 5,272,137 | 12/1993 | Blase et al. | 514/54 |
| 5,288,500 | 2/1994 | Ibsen | 424/489 |
| 5,409,907 | 4/1995 | Blase et al. | 514/54 |
| 5,534,263 | 7/1996 | Wong et al. | 424/473 |

FOREIGN PATENT DOCUMENTS

WO 85/04589  10/1985  WIPO.

*Primary Examiner*—Michael P. Woodward
*Assistant Examiner*—Brenda Glass Brumback
*Attorney, Agent, or Firm*—J. W. Routh

[57] ABSTRACT

A pharmaceutically acceptable liquid suspension system is provided for solid finely divided pharmaceutical actives incompletely soluble in water, the suspension system comprising water, xanthan gum and hydroxypropyl methylcellulose.

25 Claims, No Drawings

PHARMACEUTICAL SUSPENSION SYSTEMS

BRIEF DESCRIPTION OF THE INVENTION

The present invention is directed to pharmaceutically acceptable liquid excipient suspension systems for homogeneously suspending finely divided pharmaceutically active compounds without excessive foam formation during their preparation, such suspensions being especially useful as pediatric and/or geriatric formulations. More particularly the liquid excipient suspension systems comprise water and as the suspending agents xanthan gum and hydroxypropyl methylcellulose.

The invention is further directed to medicinal compositions comprising the claimed liquid excipient suspensions and the finely divided solid pharmaceutically active compounds suspended therein.

BACKGROUND OF THE INVENTION

Pharmaceutically acceptable liquid excipient suspension systems are well known in the art. A typical system is described in U.S. Letters Patent Nos. 5,272,137 and 5,409,907 to C. M. Blase et al. as including a substantially water soluble pharmaceutical active, e.g., acetaminophen; a suspension stabilizing effective amount of xanthan gum and microcrystalline cellulose, taste masking compositions and water.

Although liquid excipient suspension systems and their many ingredients are well known, suspension systems still present challenges to one skilled in the art to provide better homogeneously stable products as well as more efficient processes of manufacture.

SUMMARY OF THE INVENTION

The present invention provides a pharmaceutically acceptable liquid excipient suspending base for homogeneously suspending solid pharmaceutically active compounds without excessive foam formation. The excipient base comprises water, xanthan gum and hydroxypropyl methylcellulose, the xanthan gum being present in an amount of about 0.3 to about 0.5 grams per 100 milliliters of excipient base, the hydroxypropyl methylcellulose being present in an amount of about 0.3 to about 0.5 grams per 100 millileters of excipient base, and the ratio of xanthan gum to hydroxypropyl methylcellulose being about 0.88 to about 1.1:1.

Among the benefits provided by the invention is the capability of the excipient suspending base to be admixed with the finely divided solid pharmaceutical active without causing floculation or foaming especially in batches greater than 10 liters. This is important during manufacturing because it eliminates the need for deaeration of the final batch and eliminates foaming when filling bottles. The latter is important in providing even doses of medication, for example, per spoonful, since finely divided medicament may be trapped in the foam. Also, both xanthan gum and hydroxypropyl methyl cellulose are non-ionic materials and do not react with other ingredients of the suspension system or with the pharmaceutically active materials incorporated therein.

DETAILED DESCRIPTION OF THE INVENTION

The pharmaceutically acceptable liquid excipient suspending systems of the invention for homogeneously suspending solid finely divided pharmaceutically active compounds are those having an aqueous base having incorporated therein xanthan gum and hydroxypropyl methylcellulose. The xanthan gum is an article of commerce and is marketed by R. T. Vanderbilt Company, Inc. of Los Angeles, Calif. under the tradename Rhodigel 23. It is a food grade thickener in powder form of about 80 mesh. Other suitable xanthan gums are described in column 2 of the U.S. Patents cited above, i.e., U.S. Pat. Nos. 5,272,137 and 5,409,907 which are incorporated herein by reference. The xanthan gum used in the specific examples was Keltrol™.

The hydroxypropyl methylcellulose useful in the invention are those National Formulary or U.S.P. food grade products such as USP Substitution Types 2208, 2906 and 2910. These USP grades have a methoxyl content of 19–30%, a hydroxypropoxyl content of 7–12% and a molecular weight of approximately 86,000. Other suitable hydroxypropyl methylcellulose products are described in U.S. Pat. No. 4,851,232 at columns 5 and 6 herein incorporated by reference.

The xanthan gum is present in an amount of about 0.3 to about 0.5, preferably 0.4, grams per 100 milliliters of liquid suspension system. The hydroxypropyl methylcellulose is present in an amount of about 0.3 to about 0.5, preferably 0.4 grams per 100 milliliters of liquid suspension system. The ratio of hydroxypropyl methylcellulose to xanthan gum is about 0.7 to 1.2:1, preferably 0.88 to 1.1:1.

The liquid excipient suspending systems and the pharmaceutical compositions made therefrom should have an acidic pH of about 4–6.0 since slightly acidic materials are easier to preserve and are more stable.

The pharmaceutically active compounds useful in the practice of the present invention include antihistamines, decongestants, antitussives, expectorants, non-steroidal anti-inflammatory drugs (NSAIDs) and other analgesic drugs such as acetominophen and phenacetin. These materials are incorporated into the claimed liquid excipient base in amounts governed by the solubility of the material in such excipient base and such that conventional dosages thereof shall be in compliance with applicable FDA regulations. For example, materials highly soluble in the liquid excipient base must not be incorporated to the extent that a typical dose (such as one teaspoon) contains more of such material than permitted by such regulations.

Among the antihistamines useful in the practice of the present invention (along with their preferred salt form) are chlorpheniramine (maleate), brompheniramine (maleate), dexchlorpheniramine (maleate), dexbrompheniramine (maleate), triprolidine (HCl), diphenhydramine (HCl), doxylamine (succinate), tripelennamine (HCl), cyproheptatine (HCl), bromodiphenhydramine (HCl), phenindamine (tartrate), pyrilamine (maleate, tannate) and azatadine (maleate).

The antitussives useful in the practice of the present invention (along with their preferred salt form) are caramiphen (edisylate), dextromethorphan (HBr) and codeine (phosphate, sulfate).

The decongestants useful in the practice of the present invention (along with their preferred salt form) are pseudoephedrine (HCl), phenylpropanolamine (HCl) and phenylephrine (bitartrate, tannate, HBr, HCl). Phenylpropanolamine (HCl) has been found to be unsuitable for use in the present invention if high fructose corn syrup sweetener is present. Therefore, if phenylpropanolamine HCl is used in conjunction with a sweetener, a sweetener such as sorbitol should be employed.

The expectorants useful in the practice of the present invention (along with their preferred salt form) are terpin hydrate, guaifenesin (glyceryl guaiacolate), potassium (iodide, citrate) and potassium guaicolsulfonate.

The non-steroidal anti-inflammatory drugs (NSAIDs) for use in the practice of the present invention may be selected from any of the following categories:

(1) propionic acid derivatives;
(2) acetic acid derivatives;
(3) fenamic acid derivatives;
(4) biphenylcarboxylic acid derivatives; and
(5) oxicams.

Of the propionic acid derivatives for use herein, ibuprofen, naproxen, ketoprofen, flurbiprofen, fenoprofen, suprofen, fenbufen, and fluprofen may be mentioned as preferred compounds.

Of the acetic acid derivatives for use herein, tolmetin sodium, zomepirac, sulindac and indomethacin are included.

Of the fenamic acid derivatives for use herein, mefenamic acid and meclofenamate sodium are included.

Diflunisal and flufenisal are biphenylcarboxylic acid derivatives.

The oxicams include piroxicam, sudoxicam and isoxicam.

Of course, it will be appreciated by those skilled in the art, that any of the foregoing compounds may be utilized in the form of their pharmaceutically acceptable salt forms, e.g. —COO'Na$^+$, —COO'K$^+$, and the like.

Of the foregoing NSAIDs, ibuprofen and naproxen are the most preferred.

Other analgesic compounds useful in the practice of the present invention include acetominophen and phenacetin.

Of the pharmaceutically active compounds described above, those which are particularly preferred are set forth below along with preferred ranges for their inclusion into the claimed liquid excipient base.

Guaifenesin may be present in amounts of up to 300 milligrams per 5 mls. of the excipient base. Preferably, guaifenesin is present in amounts of about 10 to about 300 milligrams per 5 mls. of the excipient base. Most preferably, guaifenesin is present in amounts of about 100 to about 200 milligrams per 5 mls. of the excipient base.

Dextromethorphan may be present in amounts of between about 5 and about 20 milligrams per 5 mls. of the excipient base. Most preferably, dextromethorphan is present in amounts of about 10 to about 15 milligrams per 5 mls. of the excipient base.

Brompheniramine may be present in amounts of between about 0.5 and about 4.0 milligrams per 5 mls. of the excipient base. Most preferably, brompheniramine is present in amounts of about 2.0 milligrams per 5 mls. of the excipient base.

Pseudoephedrine may be present in amounts of between about 10 and about 60 milligrams per 5 mls. of the excipient base. Most preferably, pseudoephedrine is present in amounts of about 1 5 to about 30 milligrams per 5 mls. of the excipient base.

Acetaminophen may be present in amounts of up to about 600 milligrams per 5 mls. of the excipient base. Preferably, acetaminophen is present in amounts of about 50 to about 200 milligrams per 5 mls. of the excipient base. Most preferably, acetaminophen is present in amounts of about 150 to about 175 milligrams per 5 mls. of the excipient base.

Ibuprofen may be present in amounts of up to about 150 milligrams per 5 mls. of the excipient base. Preferably, it is present in amounts of between about 50 and about 150 milligrams per 5 mls. of the excipient base. Most preferably, ibuprofen is present in amounts of about 100 milligrams per 5 mls. of the excipient base.

Naproxen may be present in amounts of about 50 to about 250 milligrams per 5 mls. of the excipient base. Preferably, it is present in amounts of between about 100 and about 150 milligrams per 5 mls. of the excipient base.

Excipients useful in the practice of the present invention are those known to the art. These include humectants such as glycerin and propylene glycol, preservatives such as sodium benzoate and paraben, sweeteners such as sodium saccharin, corn syrup and sorbitol solutions, menthol and various flavoring and coloring agents.

The pharmaceutically active compounds and excipients should be of N.F. or U.S.P. grade.

The pharmaceutically acceptable compositions of the invention can typically have a pH of about 4 to about 5.5, a specific gravity of about 1.18 to about 1.24 and a viscosity at 25° C., using Spindle 3, and 50 rpm of 700–1650 cps.

The xanthan gum used in the specific examples was Keltrol Food Grade.

The hydroxypropyl methyl cellulose was U.S.P. Grade 2208 from Dow Chemical Company, Midland, Mich. as METHOCEL Premium Product Grade K4MP having a methoxyl content of 19–24%, a hydroxypropyl content of 7–12 and a Nominal Viscosity, 2% in water, of 4000.

The invention will now be described with respect to the following specific examples. In the examples, "APAP" stands for acetaminophen, "BPM" stands for brompheniramine maleate, "PSE" for pseudoephedrine and "EDTA" for ethylene diamine tetracetic acid. The viscometer used in the examples was a Brookfield Model DV II Viscometer.

| Ingredients | Amt/5 ml | % | Quantity |
|---|---|---|---|
| APAP (Reg) USP | 160.00 mg | 3.20 | 16.00 gms |
| BPM, USP | 1.00 mg | 0.02 | 0.10 gms |
| PSE HCl, USP | 15.00 mg | 0.30 | 1.50 gms |
| Methocel K4M Prem | 17.50 mg | 0.35 | 1.75 gms |
| Xanthan Gum, NF | 25.00 mg | 0.50 | 2.50 gms |
| Sucrose (Beet) NF | 0.50 gms | 10.00 | 50.00 gms |
| Polysorbate 80 | 5.00 mg | 0.10 | 0.50 gms |
| H. F. Corn Syrup 55% | 2.00 ml | 40.00 | 200.00 ml |
| Sorbitol Soln, USP | 0.50 ml | 10.00 | 50.00 ml |
| Glycerin, USP | 0.50 ml | 10.00 | 50.00 ml |
| Propylene Glycol, USP | 0.10 ml | 2.00 | 10.00 ml |
| Methyl Paraben, NF | 8.00 mg | 0.16 | 0.80 gms |
| Propyl Paraben, NF | 2.00 mg | 0.04 | 0.20 gms |
| Potassium Sorbate, NF | 5.00 mg | 0.10 | 0.50 gms |
| Disodium EDTA, USP | 2.50 mg | 0.05 | 0.25 gms |
| Maltol - FCC, Veltol | 0.375 mg | 0.0075 | 0.037 gms |
| D & C Red #33 | 0.075 mg | 0.0015 | 0.75 ml (1% Sol) |
| F.D & C Blue #1 | 0.016 mg | 0.00032 | 0.16 ml (1% Sol) |
| Flavor Art. Grape | 26.75 µl | 0.535 | 2.675 ml |
| Flavor Art. grape | 8.75 µl | 0.175 | 0.875 ml |
| Flavor Art. Sweet Sugar | 7.50 µl | 0.15 | 0.75 ml |
| Water Purified | Q.S. | Q.S. to 100 | 500.00 ml |

Into a beaker were placed 125 ml of water (25% of the total water). The xanthan gum was added and hydrated by mixing with a Lightnin mixer for 20 minutes at 800–900 rpm. Into a larger beaker, also equipped with a stirrer, were added the corn syrup and sorbitol, then the Polysorbate 80 followed by the acetaminophen (APAP), and mixed for 30 minutes at 500–600 rpm.

The xanthan gum premix in the first beaker was then added to the bulk in the larger beaker and mixed for 5 minutes at 700 rpm.

The sucrose was then added gradually and mixed for 30 minutes at 1200–1300 rpm until it dissolved.

In another small beaker, add 20 ml of water and dissolve therein the disodium EDTA, the brompheniramine maleate (BPM) and the pseudoephedrine hydrochloride (PSE) in order ensuring that each is well mixed before addition of the other. This premix was then added to the bulk and mixed for 10 minutes at 700–800 rpm.

The Maltol—FCC and potassium sorbate were dissolved and added to the bulk while mixing for 5–10 minutes at 700–800 rpm.

The parabens were dissolved in the propylene glycol and added to the bulk and mixed for 5 minutes at 700–800 rpm.

The Methocel K4M was dispersed in the glycerin and gradually added to the bulk while mixing for 20–30 minutes at 1000–1200 rpm.

The colors and flavors were added and mixed for 5 minutes at 700–800 rpm. Water Q.S. to 500 ml was added and mixed for 5 minutes.

The initial pH was 5.50 and this was adjusted to 5.06 by addition of 1.5 ml of a 5% citric acid solution.

The next day the resulting formulation had a spindle #3 viscosity at 20 rpm of 2870 cps and a spindle #3 viscosity at 50 rpm of 1740 cps.

The batch had no foam or flocculation but had specks of APAP on the surface. The material flowed with a uniform syrup like consistency.

| Ingredients | Amt/5 ml | % | Quantity |
| --- | --- | --- | --- |
| APAP (Reg), USP | 160.00 mg | 3.20 | 1.60 kg |
| BPM, USP | 1.00 mg | 0.02 | 10.00 gms |
| PSE HCl, USP | 15.00 mg | 0.30 | 150.00 gms |
| Methocel K4M | 17.50 mg | 0.35 | 175.00 gms |
| Xanthan Gum, NF | 25.00 mg | 0.50 | 250.00 gm |
| Sucrose (Beet) NF | 1.25 gm | 25.00 | 12.50 kg |
| Polysorbate 80 | 5.00 mg | 0.10 | 50.00 gms |
| H.F. Corn Syrup 55% | 1.00 ml | 20.00 | 10.00 l |
| Sorbitol Soln, USP | 0.50 ml | 10.00 | 5.00 l |
| Glycerin, USP | 0.25 ml | 5.00 | 2.50 l |
| Propylene Glycol, USP | 0.10 ml | 2.00 | 1.00 l |
| Methylparaben, NF | 8.00 mg | 0.16 | 80.00 gm |
| Propylparaben, NF | 2.00 mg | 0.04 | 20.00 gm |
| Potassium Sorbate, NF | 5.00 mg | 0.10 | 50.00 gm |
| Disodium EDTA, USP | 2.50 mg | 0.05 | 25.00 gm |
| Maltol - FCC, Veltol | 0.375 mg | 0.0075 | 3.75 gms |
| D&C Red #33 | 0.075 mg | 0.0015 | 0.75 gms |
| FD&C Blue #1 | 0.016 mg | 0.00032 | 0.16 gms |
| Flavor Art. Grape | 26.75 µl | 0.535 | 267.50 ml |
| Flavor Art. Grape | 8.75 µl | 0.175 | 87.50 ml |
| Flavor Sweet Sugar | 7.50 µl | 0.15 | 75.00 ml |
| Citric Acid, USP | 2.50 mg | 0.05 | 25.00 gms |
| Water Purified | Q.S. | Q.S. to 100 | 50.00 l |

The procedure for this formulation was essentially the same as in the previous example except that the citric acid was added to the disodium EDTA, BPM and PSE pre-mix after the PSE and the sucrose was separately dissolved in water with heating.

The pH of the formulation was 4.503 and after three days the formulation had a spindle #3 viscosity at 20 RPM of 2935 cps and a viscosity at 50 RPM of 1700 cps.

This large batch had no foam on top but white specks were seen on the surface which was probably acetaminophen (APAP).

Three days after the formulation was completed, it was stirred for one-half hour at 270 RPM. Again no flocculation or foam were observed.

EXAMPLE 3

The formulation of this example significantly differs from the first two examples in that only 0.4% xanthan gum was used instead of 0.5%.

| Ingredients | Amt/5 ml | % | Quantity |
| --- | --- | --- | --- |
| APAP (Reg) USP | 160.00 mg | 3.20 | 32.00 gm |
| BPM, USP | 1.00 mg | 0.02 | 0.20 gm |
| PSE HCl, USP | 15.00 mg | 0.30 | 3.00 gm |
| Methocel K4M | 17.50 mg | 0.35 | 3.50 gm |
| Xanthan Gum NF | 20.00 mg | 0.40 | 4.00 gm |
| Sucrose (Beet) NF | 1.75 gm | 35.00 | 350.00 gm |
| Polysorbate 80 NF | 5.00 mg | 0.10 | 1.00 gm |
| Sorbitol Soln, USP | 1.00 ml | 20.00 | 200.00 ml |
| Glycerin, USP | 0.40 ml | 8.00 | 80.00 ml |
| Propylene Glycol, USP | 0.10 ml | 2.00 | 20.00 ml |
| Methylparaben, NF | 8.50 mg | 0.17 | 1.70 gm |
| Propylparaben, NF | 1.50 mg | 0.03 | 0.30 gm |
| Potassium Sorbate, NF | 5.00 mg | 0.10 | 1.00 gm |
| Saccharin Sodium, USP | 10.00 mg | 0.20 | 2.00 gm |
| Disodium EDTA, USP | 2.50 mg | 0.05 | 0.50 gm |
| Magnasweet 110 | 5.00 mg | 0.10 | 1.00 gm |
| Citric Acid, USP | 0.60 mg | 0.012 | 0.12 gms |
| D&C Red #33 (1% soln) | 0.075 mg | 0.0015 | 1.50 ml |
| FD&C Blue #1 (1% soln) | 0.016 mg | 0.00032 | 0.32 ml |
| Flavor Art. Grape | 26.75 µl | 0.535 | 5.35 ml |
| Flavor Art. Grape | 8.75 µl | 0.175 | 1.75 ml |
| Flavor Sweet Sugar | 7.50 µl | 0.15 | 1.50 ml |
| Water Purified | Q.S. | Q.S. to 100 | 1000.00 ml |

The procedure for this formulation was essentially the same as that of Example 2 except that the xanthan gum was first dispersed in one-half of the glycerine before being hydrated in water. The pH was 5.143 and the next day the formulation had a spindle #3 viscosity at 20 rpm of 1150 cps and a viscosity at 50 rpm of 832.

EXAMPLE 4

The formulation of the invention set forth in this example had the same proportions of pharmaceutical actives, xanthan gum and hydroxypropyl methyl cellulose as examples 1 and 2. The size of the batch was much larger, i.e., 2000 gallons as was the equipment used. The procedure was essentially the same as in example 3, i.e., each of the xanthan gum and hydroxypropyl methylcellulose being separately dispersed in 80 gallons of glycerin.

| Ingredients | Amt/5 ml | Quantity |
| --- | --- | --- |
| APAP, USP | 160 mg | 242 kg |
| PSE, USP | 15 mg | 22.8 kg |
| BPM, USP | 1 mg | 1.52 kg |
| Citric Acid, USP | 0.6 mg | 908 g |
| Disodium Edetate, USP | 2.5 mg | 3.79 kg |
| Glycerin | 0.4 | 160 gal. |
| Magnasweet 110 | 5 mg | 7.6 kg |
| Methocel K4M, NF | 17.5 mg | 26.6 kg |
| Polysorbate 80, NF | 5 mg | 7.6 kg |
| Potassium Sorbate, NF | 5 mg | 7.6 kg |
| Propylene Glycol, USP | 0.10 ml | 40.0 gal. |

-continued

| Ingredients | Amt/5 ml | Quantity |
| --- | --- | --- |
| Sorbitol Solution, USP (70%) | 1.0 ml | 400 gal. |
| Flavors | 0.05 ml | 67 kg |
| Colorings | 0.91 ml | 138.3 g |
| Xanthan Gum | 20.0 mg | 30.4 kg |
| Sucrose Beet, NF | 1.75 g | 2650 kg |
| Saccharin Sodium, USP | 10 mg | 15.2 kg |
| Parabens | 10 mg | 15.18 kg |
| Purified Water | Q.S. | 2000 gal. |

The batch had no foam or flocculation that could be observed. The pH was 5.19. No specks were observed on the surface. The formulation had a spindle #3 viscosity at 50 RPM of 945 cps.

The batch was transferred to the packaging line and the batch was mixed at 170 rpm while packaging. No foam was observed in the bottle packages.

We claim:

1. A pharmaceutically acceptable excipient suspending liquid base for homogeneously suspending solid pharmaceutically active compounds without foam formation, which liquid excipient base comprises water and per 100 milliliters of said base a) about 0.3 to about 0.5 grams of xanthan gum and b) about 0.3 to about 0.5 grams of hydroxypropyl methylcellulose, the weight ratio of said xanthan gum to said hydroxypropyl methylcellulose being about 0.88 to about 1.1:1.

2. The pharmaceutically acceptable excipient suspending liquid base of claim 1 wherein the hydroxypropyl methylcellulose has a methoxyl content of 19–24%, a hydroxypropoxyl content of 7–12%, and a molecular weight of approximately 86,000.

3. The pharmaceutically acceptable excipient suspending liquid base of claim 2 where the pH is about 4 to about 6.0.

4. A pharmaceutically acceptable composition comprising (1) an excipient suspending liquid base comprising water and per 100 milliliters of said base (a) about 0.3 to about 0.5 grams of xanthan gum and (b) about 0.3 to about 0.5 grams of hydroxypropyl methylcellulose, the weight ratio of said xanthan gum to said hydroxypropyl methyl cellulose being about 0.88 to about 1.1:1, and (2) at least one finely divided solid pharmaceutically active compound selected from the group consisting of antihistamines, decongestants, antitussives, expectorants, non-steroidal anti-inflammatory drugs (NSAIDS) and analgesic drugs, said finely, divided solid pharmaceutically active compound being suspended in the excipient suspending liquid base.

5. The composition of claim 4 wherein the pharmaceutically active compound is an antihistamine selected from the group consisting of chlorpheniramine, brompheniramine, dexchlorpheniramine, dexbrompheniramine, triprolidine, diphenhydramine, doxylamine, tripelennamine, cyproheptatine, bromodiphenhydramine, phenindamine, pyrilamine and azatadine.

6. The composition of claim 5 wherein the antihistamine is brompheneramine maleate in an amount of about 0.5 to about 4 milligrams per 5 milliliters of the excipient base.

7. The composition of claim 4 wherein the pharmaceutically active compound is a decongestant selected form the group consisting of pseudoephedrine HCl, phenylpropanolamine and phenylephrine.

8. The composition of claim 7 wherein the pharmaceutically active compound is pseudoephedrine HCl in an amount of about 10 to about 60 milligrams per 5 milliliters of the excipient base.

9. The composition of claim 8 wherein the pharmaceutically active compound is pseudoephedrine HCl in an amount of about 15 to about 30 milligrams per 5 milliliters of the excipient base.

10. The composition of claim 4 wherein the pharmaceutically active compound is an expectorant selected from the group consisting of oterpin hydrate, guaifenesin, potassium iodide, potassium citrate and potassium guaicolsulfonate.

11. The composition of claim 10 wherein the expectorant is guaifenesin in an amount up to about 300 milligrams per 5 milliliters of the excipient base.

12. The composition of claim 11 wherein the guaifenesin is present in an amount of about 100 to about 200 milligrams per 5 milliliters of the excipient base.

13. The composition of claim 4 wherein the pharmaceutically active compound is an antitussive selected from the group consisting of caramiphen, dextromethorphan HBr, codeine phosphate and codeine sulfate.

14. The composition of claim 13 wherein the antitussive is dextromethorphan HBr in an amount of between about 5 and about 20 milligrams per 5 milliliters of excipient base.

15. The composition of claim 14 wherein the antitussive is dextromethorphan HBr in an amount of between about 1 0 and about 1 5 milligrams per 5 milliliters of excipient base.

16. The composition of claim 4 wherein the NSAID is selected from the group consisting of propionic acid derivatives, acetic acid derivatives, fenamic acid derivatives, biphenylcarboxylic acid derivatives and oxicams.

17. The composition of claim 16 wherein the NSAID is selected from the group consisting of ibuprofen, ketoprofen and naproxen.

18. The composition of claim 17 wherein ibuprofen is present in an amount ranging from about 50 to about 150 milligrams per 5 milliliters of excipient base.

19. The composition of claim 18 wherein ibuprofen is present in an amount ranging from about 100 to about 150 milligrams per 5 milliliters of excipient base.

20. The composition of claim 17 wherein naproxen is present in an amount ranging from about 50 to about 250 milligrams per 5 milliliters of excipient base.

21. The composition of claim 20 wherein naproxen is present in an amount ranging from about 100 to about 150 milligrams per 5 milliliters of excipient base.

22. The composition of claim 4 wherein the analgesic is acetominophen.

23. The composition of claim 22 wherein acetominophen is present in an amount up to about 600 milligrams per 5 milliliters of the excipient base.

24. The composition of claim 23 wherein acetominophen is present in an amount of about 150 to about 175 milligrams per 5 milliliters of the excipient base.

25. The composition of claim 4 wherein the analgesic drug is acetaminophen, the decongestant is pseudoephedrine hydrochloride and the antihistamine is brompheniramine maleate.

* * * * *